United States Patent [19]
Walker et al.

[11] Patent Number: 6,091,504
[45] Date of Patent: Jul. 18, 2000

[54] METHOD AND APPARATUS FOR MEASURING GAS CONCENTRATION USING A SEMICONDUCTOR LASER

[75] Inventors: Stephen D. Walker, Boulder; Robert A. Nichols, Thornton; William A. Curnan, Boulder; Sophat Svai, Thornton, all of Colo.; James R. Braig, Piedmont, Calif.; Daniel S. Goldberger, Boulder, Colo.

[73] Assignee: Square One Technology, Inc., Boulder, Colo.

[21] Appl. No.: 09/082,662

[22] Filed: May 21, 1998

[51] Int. Cl.$^7$ .................................................. G01N 21/00
[52] U.S. Cl. .......................... 356/437; 250/343; 356/409
[58] Field of Search ................................... 356/437, 409, 356/326, 324, 325, 343, 300, 438, 439; 250/343, 341.1, 354.1, 239.09, 339.13; 372/32; 128/633, 719, 665, 667, 664; 422/84; 600/310, 407, 532, 473–480

[56] References Cited

U.S. PATENT DOCUMENTS

| | | |
|---|---|---|
| 3,805,074 | 4/1974 | McCormack . |
| 4,730,112 | 3/1988 | Wong . |
| 5,047,639 | 9/1991 | Wong . |
| 5,134,276 | 7/1992 | Hobbs . |
| 5,267,019 | 11/1993 | Whittaker et al. . |
| 5,384,640 | 1/1995 | Wong . |
| 5,448,071 | 9/1995 | McCaul et al. . |
| 5,570,697 | 11/1996 | Walker et al. . |
| 5,625,189 | 4/1997 | McCaul et al. . |
| 5,636,035 | 6/1997 | Whittaker et al. . |

OTHER PUBLICATIONS

Bowse "Dual Modulation Laser Locking Scheme" 1991 Optical Society of America pp. 2–4.

Kroll, et al., "Measurement of gaseous oxygen using diode laser spectroscopy," *Appl. Phys. Lett.* vol. 51, No. 18, Nov. 1987, pp. 1465–1467.

Winn Hardin, "Eco–Optics: Remote Sensing Keeps Industry Clean," *Photonics Spectra*, Apr. 1998, pp. 102–106 and 108–109.

Herbert Kaplan, "Optimizing Combustion Efficiency," *Photonics Spectra*, Apr. 1998, pp. 57–58.

Giboney, et al., "The ideal light source for datanets," IEEE Spectrum, Feb. 1998, pp. 43–53.

Dr. Michael Ettenberg, "Fundamentals of Semiconductor Lasers," *Photonics Spectra*, Feb. 1998, pp. 148–150 and 152–153.

*Primary Examiner*—K. P. Hantis
*Attorney, Agent, or Firm*—Woodcock Washburn Kurtz Mackiewicz & Norris LLP

[57] ABSTRACT

A system and method for determining the concentration of an analyte such as oxygen in an unknown gas sample. A Vertical Cavity Surface Emitting Laser (VCSEL) is used as a variable wavelength light source which is "swept" through a wavelength range by varying the drive signal applied thereto. Quantitative spectroscopic analysis of the unknown gas sample is performed without the requirement of feedback circuitry for tuning the light source to the characteristic frequency of an analyte. Instead, the VCSEL is repeatedly "swept" through a range of frequencies determined by the drive signal, and the absorption is measured by the detector. The absorption lines do not always occur at the same place but instead move along around during the sweep based on the temperature and baseline current. The absorption at a particular wavelength may be determined by overlaying the drive signal and its timing information over the detected absorption signal.

19 Claims, 8 Drawing Sheets

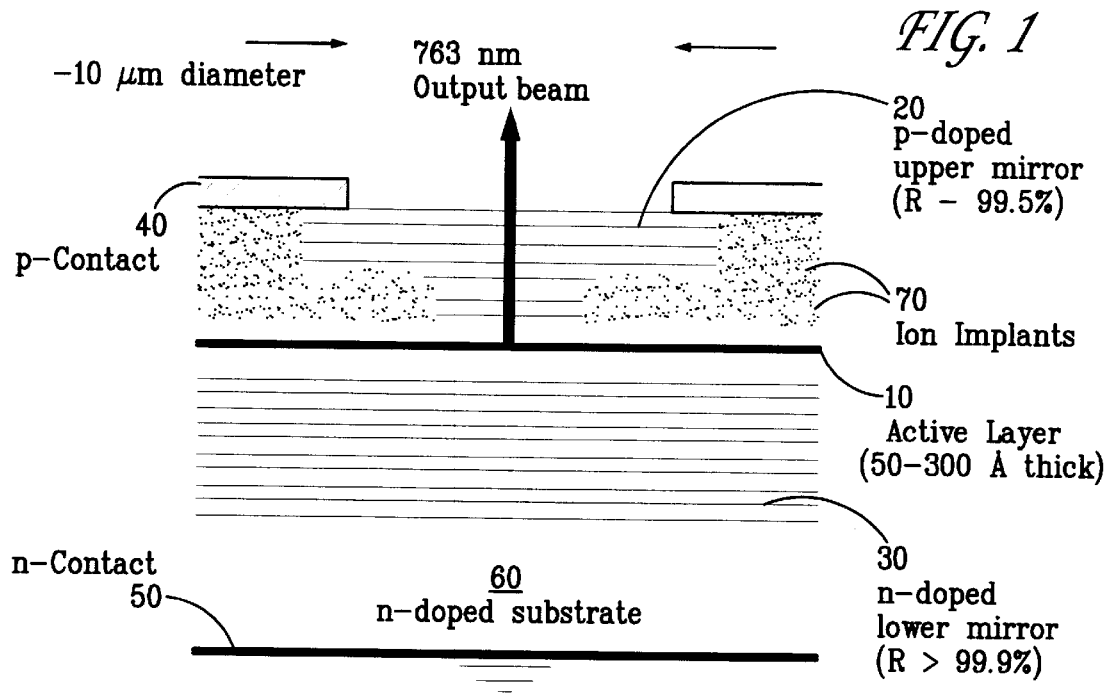
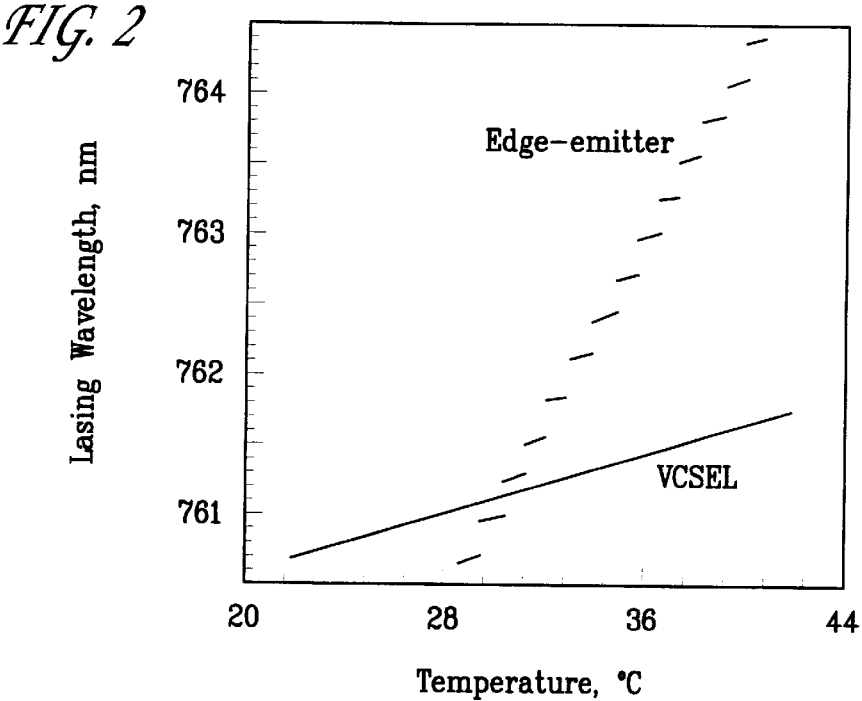

| Molecule | $\lambda$, $\mu$m | Line Strength $cm^2 mol^{-1} cm^{-1}$ | $\gamma$, $cm^{-1}$ | C x L |
|---|---|---|---|---|
| $CO_2$ | 1.573 | $1.6 \times 10^{-23}$ | 0.06 | 4.7 |
| CO | 1.567 | $2.3 \times 10^{-23}$ | 0.066 | 3.6 |
| $NO_2$ | 0.8 | $5.0 \times 10^{-23}$ | 0.073 | 1.8 |
| $CH_4$ | 1.651 | $8.7 \times 10^{-22}$ | 0.05 | 0.07 |
| $O_2$ | 0.761 | $7.71 \times 10^{-24}$ | 0.056 | 9.1 |
| HCl | 1.747 | $1.2 \times 10^{-20}$ | 0.092 | 0.010 |
| HBr | 1.341 | $2.1 \times 10^{-23}$ | 0.08 | 4.8 |
| HF | 1.330 | $1.3 \times 10^{-20}$ | 0.033 | 0.003 |
| HI | 1.541 | $3.1 \times 10^{-22}$ | 0.06 | 0.24 |
| $H_2S$ | 1.578 | $1.3 \times 10^{-22}$ | 0.175 | 1.7 |
| $NH_3$ | 1.544 | $3.7 \times 10^{-22}$ | 0.06 | 0.20 |
| $H_2O$ | 1.365 | $2.1 \times 10^{-20}$ | 0.095 | 0.006 |

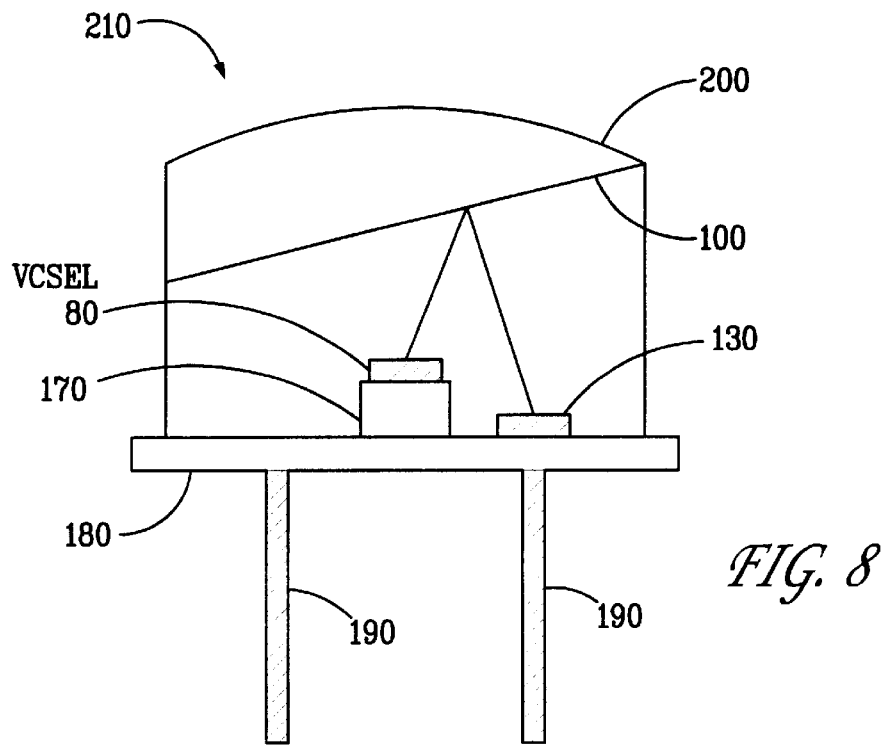
FIG. 8
FIG. 9
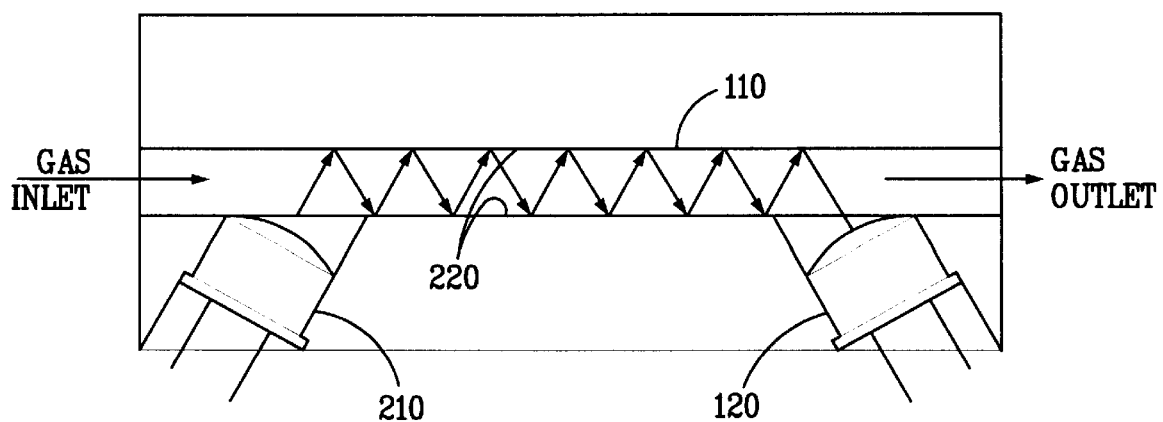

METHOD AND APPARATUS FOR MEASURING GAS CONCENTRATION USING A SEMICONDUCTOR LASER

BACKGROUND OF THE INVENTION

1. Field of the Invention

The present invention relates to a method and apparatus for measuring the concentration of gases using characteristic absorption techniques and, more particularly, to a method and apparatus for using a semiconductor laser as a variable wavelength light source for performing quantitative spectroscopic analysis of an unknown mixture of gases containing one or more analytes.

2. Description of the Prior Art

Generally, two different types of light sources have been used to measure the concentration of important analytes, such as oxygen, in a gas sample using characteristic absorption techniques whereby the irradiating light is absorbed at characteristic frequencies of one or more analytes in proportion to the amount of the analytes in the gas sample. The first type of light source is a broadband light source which illuminates the gas sample and is "tuned" to the desired characteristic absorption frequency by passing the light output through a narrowband filter "tuned" to the characteristic absorption frequency of the analyte of interest. However, such broadband light sources are generally undesirable for measuring oxygen concentration at 760 nm because such a system does not yield sufficient intensity modulation to make feasible an absorption technique for the detection of oxygen. Nevertheless, it is desired to measure the absorption of oxygen in the "A" region because no other gases are known to have spectral signatures in this region, thus minimizing interference. Accordingly, systems for measuring oxygen concentration typically use the second type of light source, which uses a narrowband light source such as a single mode or multi-mode laser precisely tuned to emit light in a narrow wavelength range about the desired absorption wavelength. However, such lasers are temperature dependent and, as a result, the temperature of the laser must be very precisely controlled to maintain the light output in the desired wavelength range. Unfortunately, large heat sinks are typically required for this purpose, which adds greatly to the bulk and expense of the light source. Also, even with such large heat sinks, precise control of the temperature, and hence the frequency of the light emitted by the laser light source, remains difficult.

An example of a system using a narrowband "tuned" light source is described by Kroll et al. in an article entitled "Measurement of Gaseous Oxygen Using Diode Laser Spectroscopy," *Applied Physics Letters*, Vol. 51, No. 18, Nov. 2, 1987, pp. 1465–67. Kroll et al. therein describe methods for using semiconductor lasers for gas spectroscopy and specifically for detecting the absorption of individual rotational lines of the A band of gaseous atmospheric oxygen in the spectral region of 760–770 nm and outputting a signal that is proportional to the $O_2$ partial pressure. Kroll et al. use a "single" frequency laser with a nominal linewidth which is approximately 1% of the $O_2$ linewidth and electronically scan the mode wavelength through individual rotational lines of the band and then measure the change in the light absorption. The light source is a laser diode with a nominal operating wavelength in the range of 759–764 nm which is mounted on a temperature-controlled heat sink and is driven by a current supply that provides DC bias, an adjustable 0–0.6 mA peak-to-peak sinusoidal modulation at 5 kHz, and an adjustable 0–1.2 mA ramp at 5 Hz. The output of the laser diode is collimated by a microscope objective, passed through the sample to be measured, and focused on a photodiode detector. During operation, the diode heat-sink temperature is slowly raised from 25° C. to 40° C. to produce a thermal scan. The thermal scan produces a discontinuous wavelength scan of approximately 30 Angstroms that covers the wavelength range containing several oxygen absorption lines. A particular line is examined by stopping the thermal scan and stabilizing the heat-sink temperature at the present level. Kroll et al. also suggest that the third derivative of the intensity of the photodiode detector can be used to derive an error signal to lock the laser frequency to $O_2$ absorption line centers. Unfortunately, maintaining the heat-sink temperature at a given level, and hence maintaining the output at a constant wavelength, is quite difficult, as is locking the laser frequency using feedback techniques.

In U.S. Pat. No. 4,730,112, Wong describes a system which also uses a narrowband light source (laser diode); however, Wong further requires a reference filter with a narrow rejection (or transmission) band centered at the wavelength of interest. In particular, Wong describes a conventional oxygen measurement system which uses a tunable diode laser, such as a distributed feedback diode laser, whose emission wavelength is adjacent to but spaced from the wavelength of a distinct absorption line. The laser diode's drive current is altered in a feedback arrangement so that the junction temperature of the laser diode is changed, thereby changing the wavelength of the emitted radiation and, in effect, scanning the emitted radiation through a range of wavelengths that includes the absorption line of interest. The reference filter is used to assure that the laser light source locks onto the correct spectral feature so that the laser diode can be "locked" onto the characteristic absorption line for oxygen. A very limited amount of tuning of the laser is possible by varying the temperature of the diode laser as proposed by Wong, and, in any case, a very elaborate temperature control system is required to control the temperature to an accuracy of less than 0.05° C. in order to select a wavelength within the few tenths of an Angstrom accuracy needed for gas spectrometry.

Wong further describes in U.S. Pat. No. 5,047,639 a concentration detector which uses a feedback loop to lock a single mode diode laser onto the chemical absorption peak of the analyte of interest. The diode laser purportedly produces a spectral distribution having a single peak of width comparable to the linewidth of the spectral lines in the gas being detected and is controlled to be coincident with one of the spectral lines in the gas being detected. As in the Wong '112 patent, the wavelength of the diode laser is controlled by controlling the drive current to the diode laser so as to control the temperature of the diode laser. The feedback loop varies the drive current until the wavelength of the diode laser is centered on an absorption peak of the reference gas component. The feedback loop includes dithering circuitry that produces a first harmonic component signal that is used to lock the laser wavelength to the center wavelength of the absorption peak of the reference gas and produces a second harmonic component signal that indicates whether the laser wavelength lies within an absorption peak. At device turn on, a ramp signal tunes the wavelength until the second harmonic signal indicates that the laser wavelength lies within an absorption peak. However, as with the Wong '112 system, a complicated feedback arrangement is required to "lock" the laser output to the wavelength of the absorption peak of the reference gas.

McCaul et al. describe in U.S. Pat. Nos. 5,448,071 and 5,625,189 an on-airway gas spectroscopy device which, as in the Wong systems, includes a tunable laser diode. However, in the McCaul et al. system, the laser diode is driven by a periodic stepped laser diode drive current where each period of the stepped laser diode drive current has a plurality of constant current intervals. Certain of the constant current intervals are used to lock the laser radiation emitted from the laser diode onto a preselected absorption line, while others of the constant current intervals are used to subtract baseline absorption measurements from peak constant current interval absorption measurements. By detecting absorption during the constant laser diode current intervals, McCaul et al. purport to separate the functions of subtracting baseline noise, centering radiation frequencies on the absorption line, and measuring the absorbance at the peak frequency of the absorption line. A heated sample cell is provided to allow for the measurement of oxygen concentration in human breath, where the pressure and temperature of the gas in the sample cell are detected to account for pressure and temperature dependencies of the absorption measurement. The laser light is directed through the sample cell multiple times to provide a sufficient path length for measurable oxygen absorption in the A region.

A semiconductor laser such as a vertical cavity surface emitting laser (VCSEL) is a laser which recirculates light inside the optical cavity so that the emitted light is normal to the surface of the laser. A cross-section of a conventional VCSEL is illustrated in FIG. 1. Like an edge-emitting laser, a VCSEL requires an active lightemitting layer 10 (50–300 Angstroms thick) to be sandwiched between two mirrors 20 and 30, which are, in turn, sandwiched between a p-contact 40 and an n-contact 50 separated from the lower mirror 30 by an n-doped substrate 60. However, in the case 30 of VCSELs, the mirrors 20 and 30 are part of the epitaxial layer design, and the length of the active layer 10 is four orders of magnitude shorter (typically 0.01–0.02 $\mu$m). The shorter active length requires the use of many more reflective mirrors (e.g., distributed Bragg reflectors or DBRs). Generally, the lower reflective mirrors or DBRs 30 are doped n-type (with a reflectance R>99.9%), while the upper reflective mirrors 20 are doped p-type (with a reflectance of approximately 99.5%) and include ion implants 70 so as to create a p-n junction with current flowing vertically through the device. The resulting device outputs light in wavelengths from 650 nm to 1100 nm and higher (763 nm in the example of FIG. 1).

Unlike LEDs or edge-emitting lasers, VCSELs can internally compensate their drive currents continuously over a temperature range and thus may be particularly suitable as a light source in analyte sensors. As illustrated in FIG. 2, the output wavelength of the VCSEL of FIG. 1 can be varied as a smooth function of device temperature for continuous wavelength tuning, while conventional edge emitting laser diodes exhibit mode hopping behavior in that they do not change wavelength in a smooth fashion. The wavelength change in the VCSEL occurs because of small changes in index of refraction and physical length of the resonating structures within the VCSEL.

In U.S. Pat. No. 5,570,697, Walker et al. describe an on-airway oxygen sensor which uses a VCSEL as a light source. The VCSEL is continuously tuned to emit light having a frequency linewidth of less than 3 GHz at the resonance of oxygen (in the 760 nm region) or any other analyte of interest. The VCSEL is driven by a wavelength controller which may be a resistor, thermoelectric cooler, or some similar device which can cause the laser beam wavelength to vary through an absorption resonance of the analyte of interest by varying the temperature of the VCSEL, as in the Wong et al. systems for laser diodes. Unlike conventional edge-emitting semiconductor laser diodes emitting at wavelengths shorter than 1200 nm which exhibit discrete "hops" in wavelength as the temperature or applied current is varied, the VCSEL is continuously tunable. Walker et al. tune the VCSEL to the maximum absorption line of the analyte of interest by providing electronic control circuits which correlate maximum and minimum absorption of the laser beam with the tuning signals applied to the VCSEL which produced the maximum and minimum absorptions. The VCSEL is then tuned so that it spends most of the time at a wavelength corresponding to the maximum absorption line of the analyte of interest, a lesser time at a wavelength corresponding to the nominally zero species absorption, and a minimum time at intermediate wavelengths. Alternatively, the VCSEL may be tuned using the third harmonic signal from a lock-in amplifier as described by Wong et al. Thus, as with the Wong et al. systems, a complicated feedback arrangement is required to "lock" the laser output to the wavelength of the absorption peak of the reference gas.

Thus, the basic principles of laser diode absorption spectroscopy, particularly as it applies to the measurement of gaseous oxygen, are known in the art. Walker et al. in particular discuss the benefits of using a VCSEL structure for spectroscopy. However, such prior art devices remain relatively expensive and unreliable because of the need to carefully control the temperature of the laser diode or VCSEL in order to "tune" to a particular wavelength for absorption measurements. A more reliable, less expensive way to perform laser spectroscopy in general and oxygen concentration measurements in particular is desired. Moreover, it is desired that the resulting light source be physically smaller and that it consumes less power than prior art devices. The present invention has been designed to meet these needs in the art.

SUMMARY OF THE INVENTION

The above-mentioned and other needs in the art have been met by providing an open loop laser light source which sweeps through the characteristic absorption frequency or frequencies of interest without locking onto, or "tuning" to, a particular frequency. Since no complicated feedback circuitry is required, the invention provides a more reliable, less expensive way to perform laser spectroscopy and, particularly, oxygen concentration measurements. Also, the invention is physically smaller and consumes less power than prior art devices.

In accordance with the invention, a gas analyzer is provided for detecting the concentration of a gaseous component, such as oxygen, within a gas sample in a sample cell containing an unknown concentration of the gaseous component. The gas analyzer includes a driving circuit which generates a laser driving signal preferably having a repetitive pattern, such as a sawtooth waveform. The laser driving signal is applied to the laser light source so as to vary the temperature of a lasing region of the laser light source so that the laser light source outputs laser light which is continuously varied through a range of frequencies including a characteristic absorption frequency of the gaseous component. In a preferred embodiment, the laser light source is a vertical cavity surface emitting laser (VCSEL). The continuously varying laser light is directed through the sample cell whereby laser light at the characteristic absorption frequency may be absorbed in proportion to the concentration of the gaseous component in the sample cell. A detector detects laser light in the range of frequencies which has passed through the sample cell and which has been absorbed at the characteristic absorption frequency of the gaseous component to provide a detection output which is demodulated by a compensation circuit to remove the laser driving signal so as to leave an absorption signal with characteristic absorption lines at points in the absorption signal where the laser light source outputs light at the characteristic absorption frequency of the gaseous component. Since the magnitude of the characteristic absorption lines are proportional to the concentration of the gaseous component in the gas sample in accordance with Beer's law, the concentration of the gaseous component may be readily determined.

Those skilled in the art will appreciate that the relationship between detector output and gas concentration is given by Beer's Law:

$$A = \log(I_0/I_t) = \log(1/T),$$

where:
  A=Absorbance (unitless);
  $I_0$=Original or input optical intensity (Watts);
  $I_t$=Optical intensity transmitted through sample (Watts); and
  T=Transmittance (unitless).

The absorbance (A) is directly proportional to the concentration of gas and the pathlength. Thus:

$$A = E*C*L$$

where:
  E=Extinction coefficient (liters/(mole*cm))
  L=Pathlength (cm);
  C=Concentration (moles/liter); and $$C = A/(E*L).$$

In a preferred embodiment, a compensation detector and beamsplitter are provided. The beamsplitter splits the laser light so that a first portion is directed through the sample cell and a second portion impinges upon the compensation detector. A reference signal output by the compensation detector is provided to the compensation circuit for removing a common mode signal. A processor calculates the concentration C of the gaseous component from a magnitude $V_A$ of the characteristic absorption lines and a magnitude $V_0$, where $V_0$ is the amount of light at the characteristic absorption frequency, calculated as if there is no absorbing analyte in the sample chamber, in accordance with the following equation:

$$C = X*V_A/V_0 + Y$$

where X and Y are calibration constants which are preferably stored in an electronic device such as an EEPROM.

Preferably, the sample cell is straight and provides a laminar gas flow path along a central transmission axis of the sample cell from a gas inlet to a gas outlet. In a first embodiment, the laser light source is located at an angle to the central transmission axis of the sample cell at a gas inlet end of the sample cell and the detector is located at an angle to the central transmission axis of the sample cell at a gas outlet end of the sample cell. The sample cell preferably has reflective walls whereby the continuously varying laser light is reflected by the reflective walls a plurality of times as the laser light passes through the sample cell to the detector.

In an alternative embodiment, an optical fiber carries the laser light from the laser light source to a gas inlet end of the sample cell. In such an embodiment, the detector may be located on the central transmission axis of the sample cell at a gas outlet end of the sample cell. On the other hand, a highly reflective mirror may be located on the central transmission axis of the sample cell at the gas outlet end of the sample cell and the detector located on the central transmission axis of the sample cell at a gas inlet end of the sample cell.

The laser light source is preferably mounted on a thermoelectric heater/cooler which is, in turn, mounted upon a transistor outline header. Preferably, the header includes an optically transmissive window which passes the laser light from the VCSEL to the outside of the header for direction through the sample cell. The compensation detector is also preferably located on the header and situated to receive a portion of the laser light reflected by the optically transmissive window.

The scope of the invention also includes a method of detecting the concentration of a gaseous component, such as oxygen, in a gas sample. In a preferred embodiment, such a method comprises the steps of:
  inserting an unknown concentration of the gaseous component into a sample cell;
  generating a laser driving signal;
  applying the laser driving signal to a lasing region of a laser light source to cause the laser light source to output laser light which continuously varies through a range of frequencies including a characteristic absorption frequency of the gaseous component;
  directing the continuously varying laser light through the sample cell whereby laser light at the characteristic absorption frequency may be absorbed in proportion to the concentration of the gaseous component in the sample cell;
  detecting laser light in the range of frequencies which has passed through the sample cell and which has been absorbed at the characteristic absorption frequency of the gaseous component to provide a detection output;
  demodulating the detection output to remove the laser driving signal so as to leave an absorption signal with characteristic absorption lines at points in the absorption signal where the laser light source outputs light at the characteristic absorption frequency of the gaseous component; and
  calculating the concentration C of the gaseous component in the gas sample from a magnitude $V_A$ of the characteristic absorption lines and a magnitude $V_0$, where $V_0$ is the amount of light at the characteristic absorption frequency, calculated as if there is no gaseous component in the sample cell.

The method of the invention also preferably includes the additional steps of generating a reference signal and adjusting the detection output with the reference signal so as to remove a common mode signal. Preferably, the directing step also includes the step of lengthening the optical path by reflecting the continuously varying laser light off of reflective walls of the sample cell a plurality of times as the laser light passes through the sample cell. Also, the laser light source is preferably a vertical cavity surface emitting laser (VCSEL) which is "swept" through a range of wavelengths by varying a temperature of the lasing region of the VCSEL through application of the laser driving signal.

BRIEF DESCRIPTION OF THE DRAWINGS

The above and other objects and advantages of the invention will become more apparent and more readily appreciated from the following detailed description of the presently preferred exemplary embodiment of the invention taken in conjunction with the accompanying drawings, of which:

FIG. 1 illustrates cross-section of a conventional vertical cavity surface emitting laser (VCSEL) used as a laser source in a preferred embodiment of the invention.

FIG. 2 illustrates that the output wavelength of the VCSEL of FIG. 1 can be varied as a smooth function of device temperature for continuous wavelength tuning, while conventional edge emitting laser diodes exhibit mode hopping behavior in that they do not change wavelength in a smooth fashion.

FIG. 8 illustrates a light source package in accordance with a preferred embodiment of the invention.

FIG. 9 illustrates the optical path through the gas sample cell in accordance with a presently preferred embodiment of the invention.

DETAILED DESCRIPTION OF THE PREFERRED EMBODIMENT

A system and method which meets the above-mentioned objects and provides other beneficial features in accordance with the presently preferred exemplary embodiment of the invention will be described below with reference to FIGS. 3–11. Those skilled in the art will readily appreciate that the description given herein with respect to those figures is for explanatory purposes only and is not intended in any way to limit the scope of the invention. All questions regarding the scope of the invention should be resolved by referring to the appended claims.

Figures 3, 4:
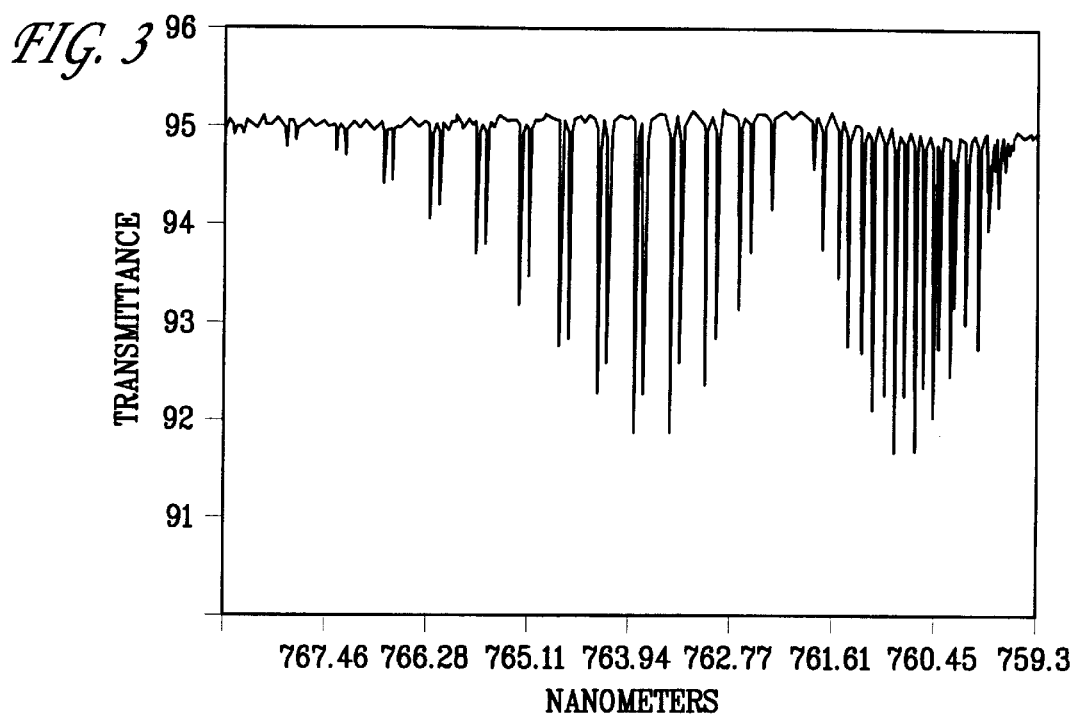
FIG. 3 illustrates a representative transmittance spectra of gaseous oxygen in the A wavelength region.
FIG. 4 is a table listing absorption wavelengths and strengths for several frequently monitored gases having spectral features in the wavelength range accessible to laser diode spectroscopy.

FIG. 3 is a representative transmittance spectra of gaseous oxygen in the A wavelength region. FIG. 3 shows the very specific pattern of absorption lines characteristic of gaseous oxygen, particularly those absorption lines around 761 nm. As noted above, the A region is desirable for measuring gaseous oxygen since no other gases of interest exhibit measurable absorption in that region. This is evidenced by the table of FIG. 4, which lists the absorption wavelengths and strengths for several other frequently monitored gases having spectral features in the wavelength range accessible to laser diode spectroscopy. In FIG. 4, $\gamma$ is the air broadened half-width at 1 atmosphere, while CxL is the concentration pathlength product of the given gas that could be detected with a signal-to-noise ratio of one under the assumption of a $10^{-6}$ absorption sensitivity.

A VCSEL is desired as a laser light source in accordance with the invention since, as noted above, the output wavelength of a VCSEL can be changed as a smooth function of electrical drive characteristics. In a preferred embodiment of an oxygen sensor developed in accordance with the invention, the VCSEL is a 763 nm (+/−5 nm at 40° C.) VCSEL laser manufactured by MicroOptical Devices, Inc. having a spectral width of less than 1 nm and a change in wavelength of the output with temperature of 0.05+/−0.015 nm/° C.

Figure 5:
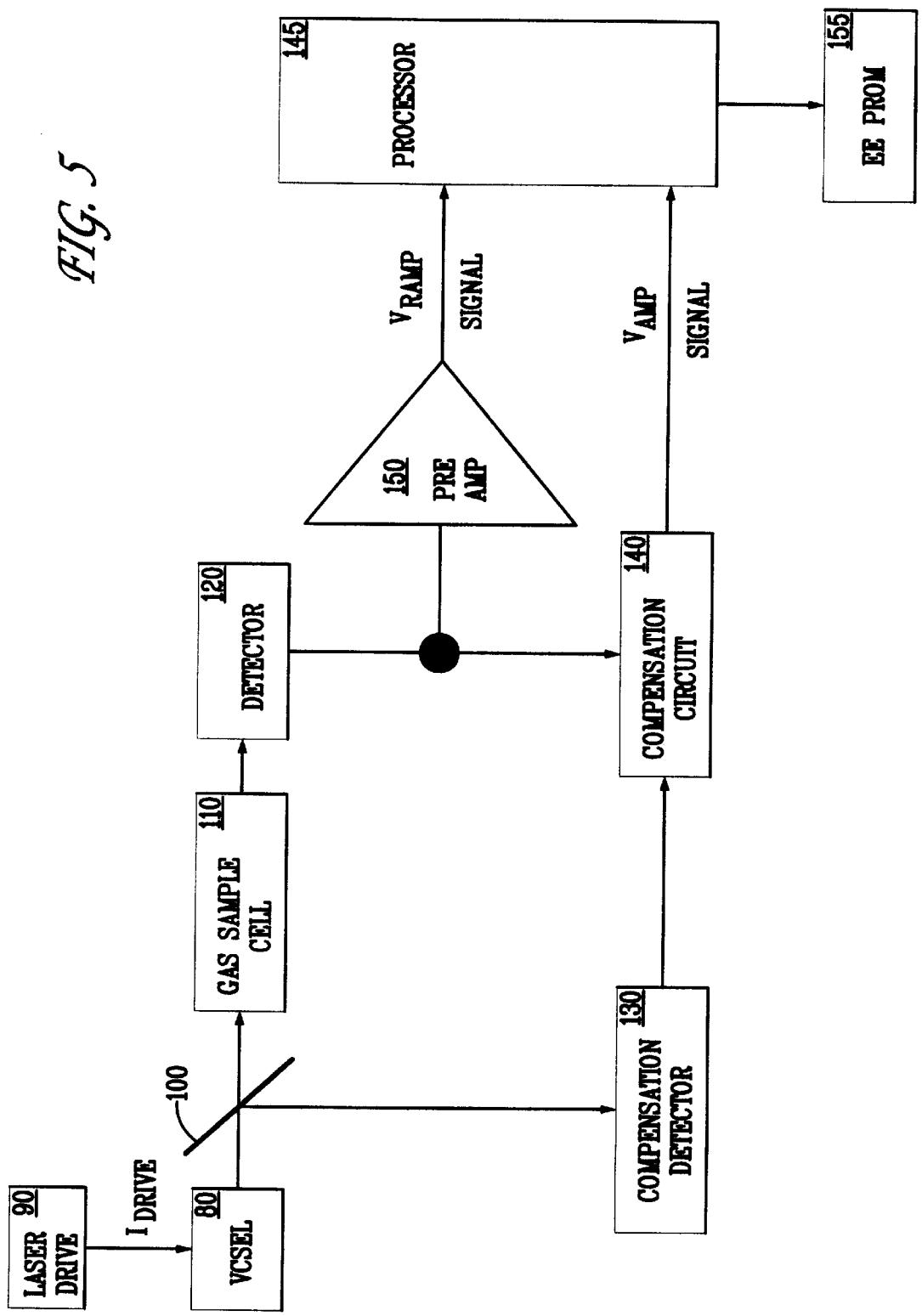
FIG. 5 illustrates a block diagram of an analyte sensor designed in accordance with the invention.
Figure 6A:
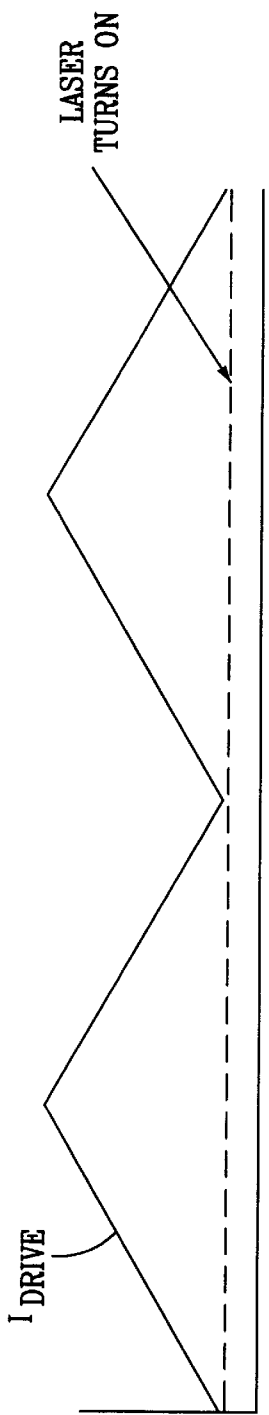
FIG. 6A illustrates the drive signal, $I_{DRIVE}$, applied to the VCSEL to cause its output to sweep through a range of wavelengths in accordance with the techniques of the invention.
Figure 6B:
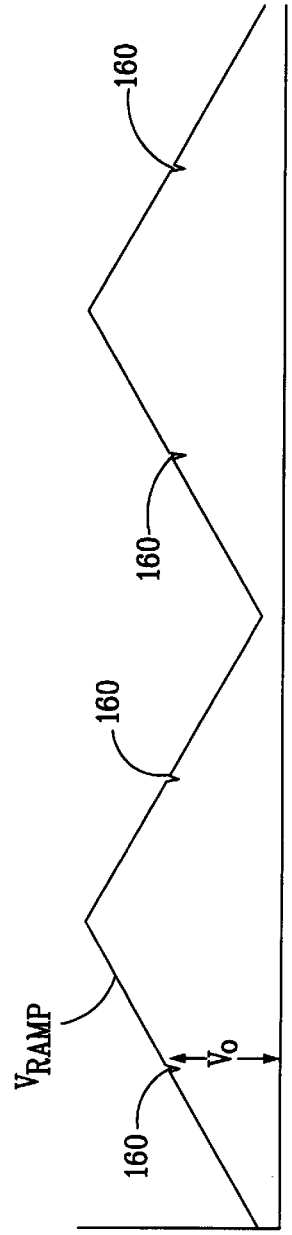
FIG. 6B illustrates the buffered signal $V_{RAMP}$ which mimics $I_{DRIVE}$ except for small paused by the analyte's absorption lines.
Figure 6C:
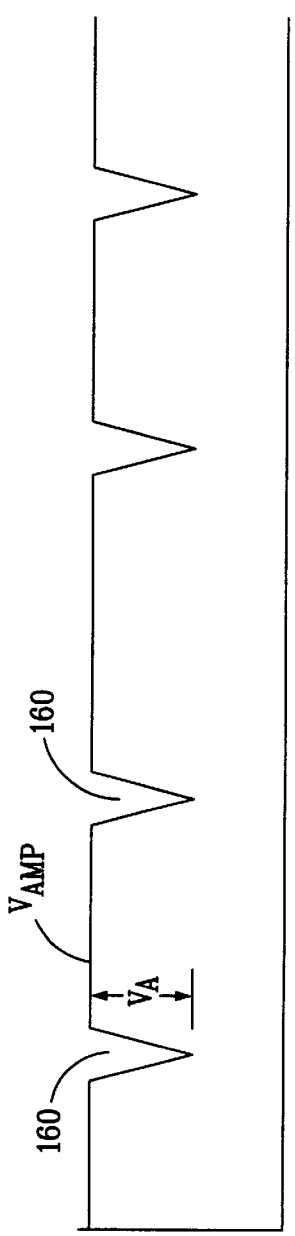
FIG. 6C illustrates the absorption signal, $V_{AMP}$, which has been demodulated from the sawtooth driving signal $I_{DRIVE}$ after the laser light has passed through the sample cell and been amplified for output.

FIG. 5 illustrates a block diagram of an analyte sensor incorporating such a VCSEL in accordance with the invention. As illustrated, the light source is a VCSEL 80 driven by a drive signal $I_{DRIVE}$ generated by a laser driving circuit 90. $I_{DRIVE}$ is preferably a variable current in a repetitive pattern, such as the sawtooth waveform shown in FIG. 6A. However, any kind of time-varying waveform may be used for $I_{DRIVE}$, and, generally, the waveform does not have to be repetitive. In accordance with the invention, laser driving circuit 90 is a signal generator which generates $I_{DRIVE}$ and applies it to the p-n junction of the VCSEL 80 so as to vary in a controlled manner the temperature of the VCSEL 80 and to thereby "sweep" the VCSEL 80 through a range of wavelengths. The resulting variable wavelength light is then passed through a beamsplitter 100, passed through a gas sample cell 110 containing the analyte whose concentration is to be measured, and applied to a detector 120. The remainder of the split light is directed to impinge directly on a compensation detector 130 for generating a reference signal. The compensation detector 130 permits the common mode signal between the two paths to be removed so that variations in absolute intensity between the two paths can be corrected. Compensation detector 130 is preferably the same as detector 120. In a preferred embodiment, detectors 120 and 130 are D series pin photodiodes available from UDT, Hawthorne, Calif. The outputs of the respective detectors 120 and 130 are applied to a compensation circuit 140 which removes the carrier waveform (sawtooth) and amplifies the perturbations 160 caused by the oxygen absorption lines. In particular, the absorption signal is demodulated from the sawtooth driving signal $I_{DRIVE}$ and is amplified and output as $V_{AMP}$ (FIG. 6C) for a determination of the concentration by processor 145. As shown in FIG. 6C, absorption having a magnitude of $V_A$ occurs at the characteristic absorption lines of the gas of interest and varies with analyte concentration in accordance with Beer's Law. Similarly, the buffered signal at detector 120 is labeled $V_{RAMP}$ and is similarly amplified by preamplifier 150 and output as $V_{RAMP}$ (FIG. 6B) for processing by processor 145, where $V_{RAMP}$ mimics $I_{DRIVE}$ except for small perturbations 160 caused by the analyte's (e.g., oxygen) absorption lines. As shown in FIG. 6B, the voltage at the characteristic absorption lines is identified as $V_O$, where $V_O$ is measured by interpolating the voltage at the point of perturbation 160 as if the perturbation 160 were not there.

Those skilled in the art will appreciate that the circuit of FIG. 5 is quite simple in that, unlike prior art systems using edge emitting lasers tuned to the characteristic absorption frequency, it requires no feedback circuitry and no heat sink. Instead, the VCSEL 80 is repeatedly "swept" through a range of frequencies determined by $I_{DRIVE}$. The absorption is measured by the detector 120 and correlated in time with the corresponding wavelengths of the VCSEL 80. As is apparent from FIGS. 6B and 6C, the perturbations 160 caused by the oxygen absorption lines do not always occur at the same place but instead move along the x axis based on the sweep rate of $V_{RAMP}$ (i.e., where $I_{DRIVE}$ sweeps through $V_0$ where $V_0$ is the amount of light at the characteristic absorption frequency of the analyte, calculated as if there is no absorbing analyte in the sample cell). The absorption at a particular wavelength may be determined by overlaying the $I_{DRIVE}$ signal and its timing information over $V_{AMP}$.

Compensation circuit 140 may be a Hobb's circuit of the type described in U.S. Pat. No. 5,134,176 which is modified for use with time varying carrier current signals. In addition, an EEPROM 155 or similar electronic component, such as a resistor, may be used to provide calibration information to processor 145 during its calculations. The EEPROM 155 is preferably provided with the VCSEL 80.

As known to those skilled in the art, the concentration of an analyte in a sample cell may be readily calculated from the Beer Lambert equation:

$$I/I_0 = e^{-\beta cL}$$

where:
I=the light intensity transmitted through the sample cell;
$I_0$=the light intensity launched into the sample cell;
β=absorption coefficient (at a specific wavelength)=1/transmittance;
c=concentration of the analyte; and
L=optical path length of the sample cell.

As also known to those skilled in the art, the concentration of n analytes may be determined by making measurements with at least n+1 discrete wavelengths.

Figure 7:
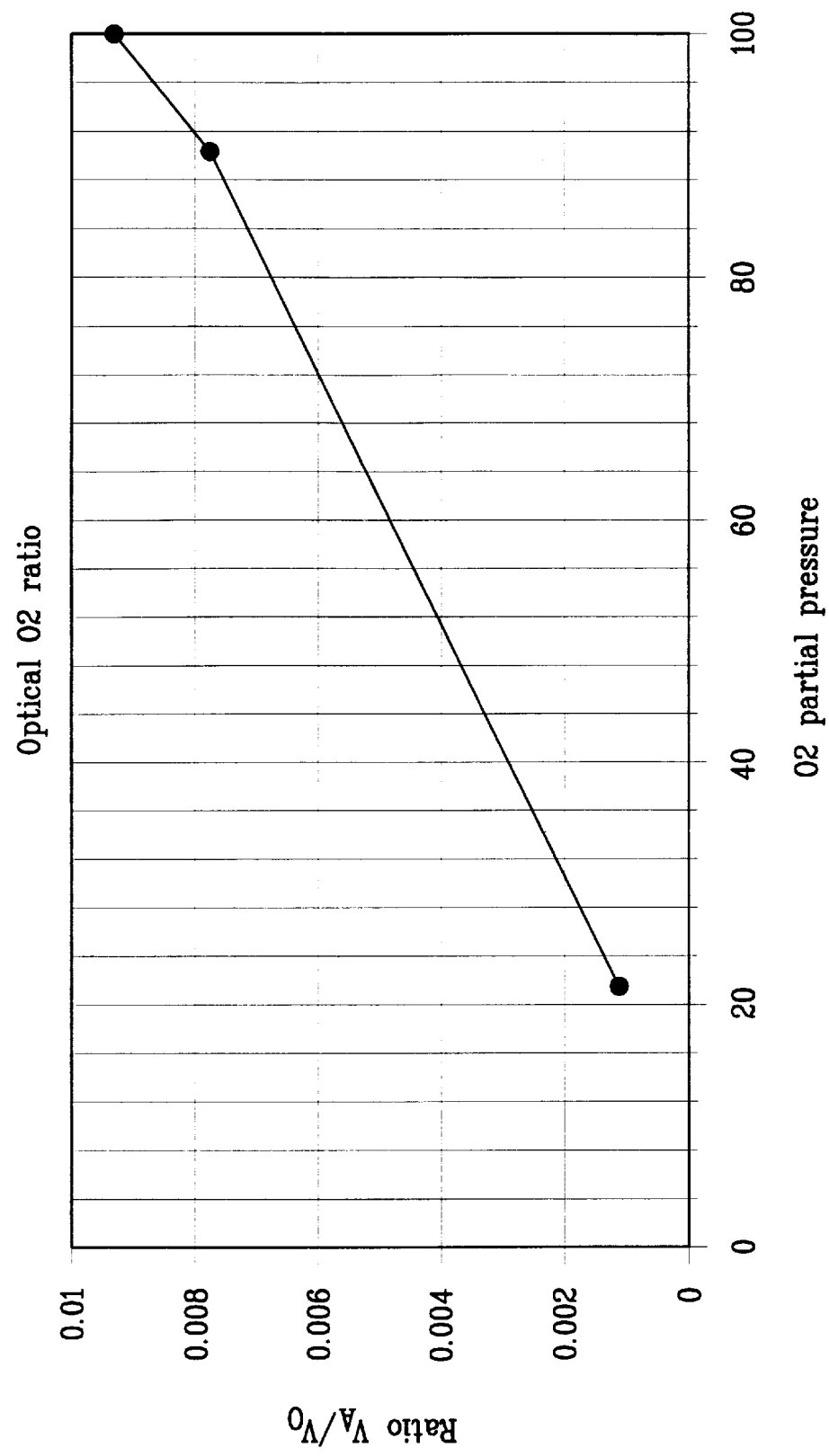
FIG. 7. illustrates the relationship between $V_A/V_O$ and the partial pressure of oxygen.

The inventors have further discovered and demonstrated that the partial pressure of oxygen (ppO$_2$) can be calculated from the voltage measurements $V_A$ and $V_0$ as follows:

$$ppO_2 = X^* V_A/V_0 + Y$$

where X and Y are calibration constants which are preferably stored in EEPROM 155. FIG. 7 shows some experimental data for $V_A/V_0$ that validates this simple mathematics. Those skilled in the art will recognize that many other formulations and signal processing algorithms may be used to find the partial pressure of oxygen or any other analyte of interest.

FIG. 8 illustrates a light source package in accordance with a preferred embodiment of the invention. As shown, an appropriate VCSEL 80 is mounted on a conventional thermoelectric heater/cooler 170 with a small temperature sensor of the type available, e.g., from Fenwal Electronics of Milford, Mass. The thermoelectric heater/cooler/sensor 170 is used to maintain the laser 80 at a fixed temperature during changes in ambient temperature over its operating range. The laser 80 and heater/cooler/sensor 170 is, in turn, mounted on a conventional transistor outline is (TO) header 180 having pins 190. A reference photodiode or compensation detector 130 is also mounted on the TO header 180 so as to accept the reflected light from lens/window 200 as illustrated. The light which passes through lens/window 200, on the other hand, is applied to the gas sample cell 110 for a gas concentration measurement. In a preferred embodiment, lens/window 200 may be convex lenses available from Edmund Scientific Company, Barrington, N.J. In accordance with the invention, the lens/window 200 serves several functions, including providing a transparent, gas tight seal, efficiently collecting and focusing most of the laser output light, and reflecting a portion of the laser output to the compensation detector 130. Preferably, the entire laser assembly 210 of FIG. 8 is hermetically sealed in an inert atmosphere, typically dry nitrogen.

The inventors have additionally discovered that the laser assembly 210 and beam steering optics must be carefully constructed so that no light can be reflected directly back onto the emission window of the laser 80. Interference patterns created by parallel surfaces in the optical path (e.g., the optical windows) can cause unstable resonance phenomena which ultimately manifest as system noise. Accordingly, it is preferred that the laser assembly 210 and the detector assembly 120 be arranged in a configuration such as that illustrated in FIG. 9 in order to prevent such interference patterns. The pneumatic/optical design of FIG. 9 preferably includes an optical path through the gas sample cell 110 which is sufficiently long enough to permit adequate analyte sensitivity and includes efficient optics to insure an adequate signal level at the detector 120. Preferably, the gas path through the gas sample cell 110 is straight with minimum discontinuities so as to provide a smooth gas flow path in order to promote laminar flow, the most efficient way to cleanly sweep residual gases from the gas sample cell 110. Also, a minimum swept volume for gas flow is preferably provided in order to decrease response time at low flow rates. These somewhat competing requirements force a variety of compromises based on the desired functional characteristics. For example, in the design of FIG. 9, the optical path length may be 6 inches in a 4 inch long physical path length. The 6 inch path length permits an oxygen resolution of about 1 mm Hg. Of course, longer paths would permit more resolution.

In addition, the walls 220 of the gas path in the gas sample cell 110 are preferably highly reflective. The inventors have found that the design of FIG. 9 has an optical throughput of roughly 50% if the walls are 95% reflective. Such reflectivity is readily achieved with polished metal, glass, or plastic surfaces.

Figure 10A:
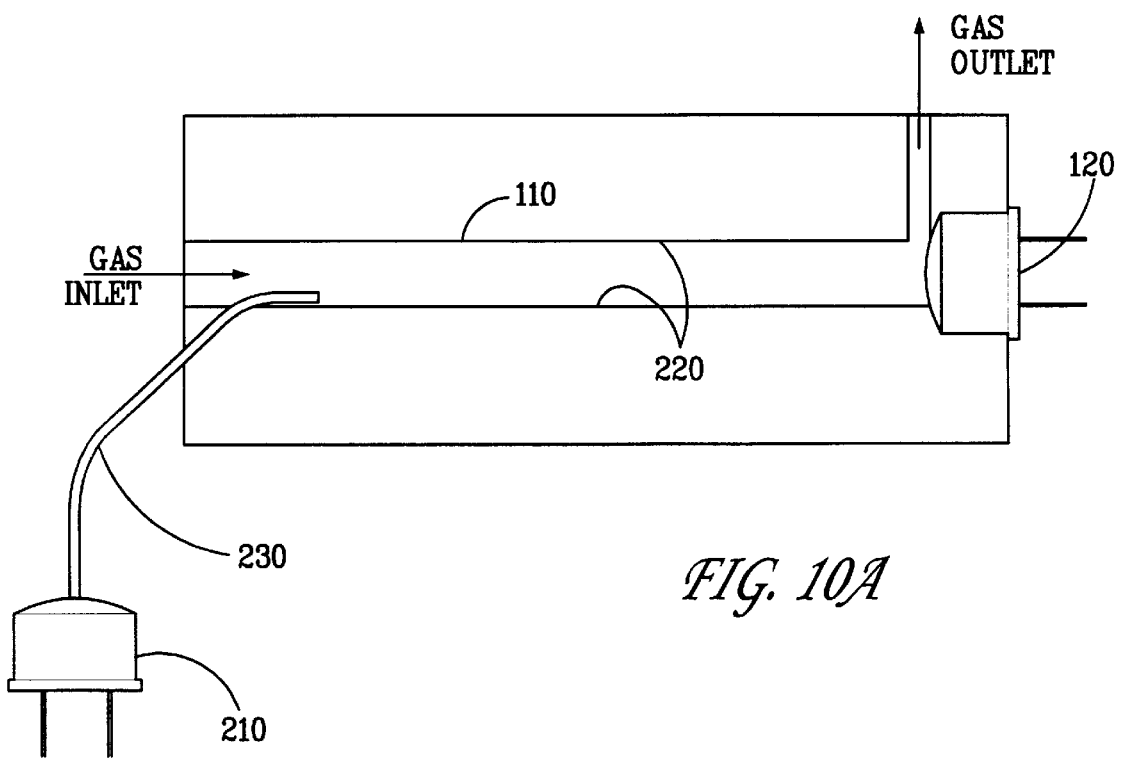
FIGS. 10A and 10B illustrate alternative embodiments of the optical path through the gas sample cell in accordance with the invention.
Figure 10B:
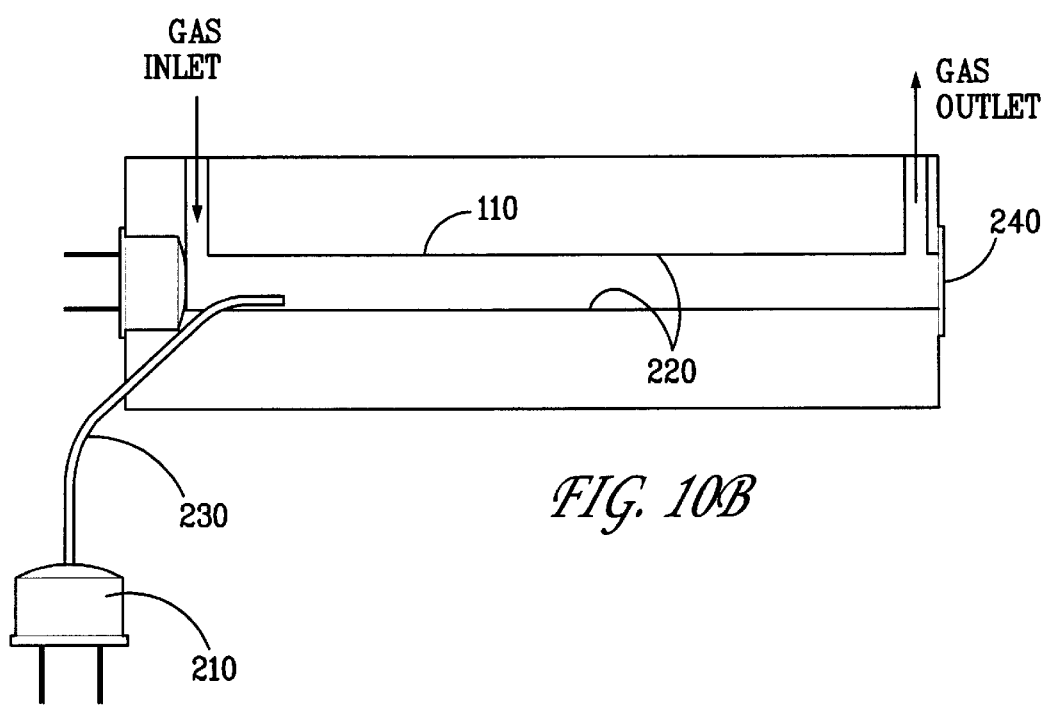

FIGS. 10A and 10B illustrate alternative embodiments of the optical path through the gas sample cell in accordance with the invention. In contrast with the embodiment of FIG. 9, the embodiments of FIGS. 10A and 10B use a fiber optic element 230 to transmit light from the laser assembly 210 into the gas sample cell 110. As shown in FIGS. 10A and 10B, the laser assembly is mounted remotely from gas sample cell 110 and fiber optic element 230 launches light into the gas sample cell 110 at a low angle (which reduces the need for highly reflective walls 220, although highly reflective walls are still desirable). In the FIG. 10A embodiment, the detector 120 may be placed on the axis of the gas sample cell 110 at its exit end instead of off-axis as in FIG. 9. This configuration makes the light collection process more efficient at the expense of a "clean" pneumatic system. On the other hand, as shown in the FIG. 10B embodiment, the detector 120 may be placed on the axis of the gas sample cell 110 at its entrance end and a highly reflective mirror 240 placed on the axis of the gas sample cell 100 at its exit end. The configuration of FIG. 10B doubles the optical path length without changing the physical size or swept volume of the gas sample cell 110.

Figure 11:
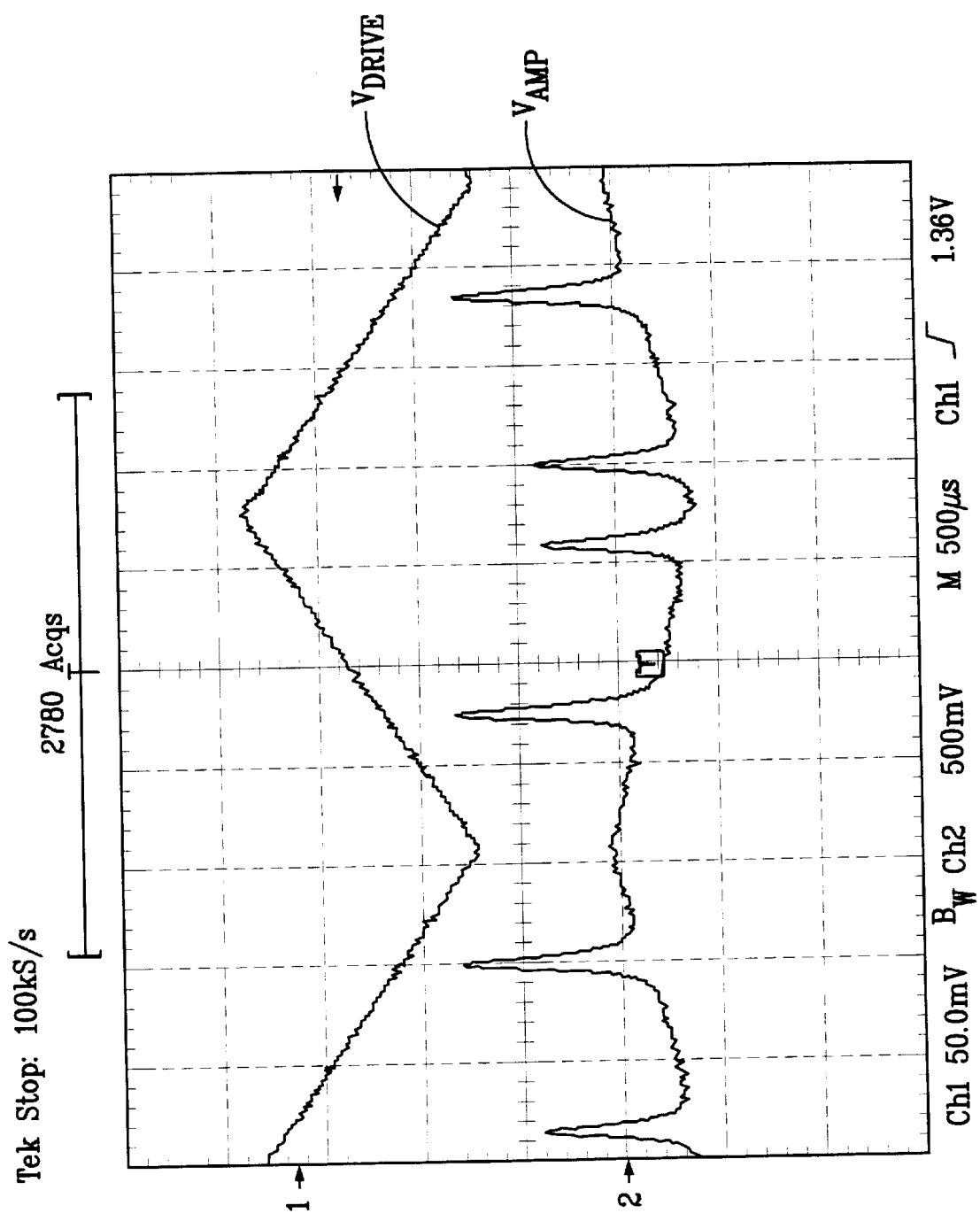
FIG. 11 illustrates the actual output of the system of the invention where the gas sample cell includes 600 mm Hg of oxygen.

Finally, FIG. 11 illustrates the actual output for a gas sample including 600 mm Hg of oxygen in the gas sample cell 110. As illustrated, pronounced absorption lines can be found in $V_{AMP}$ which can be used as described above to determine the actual oxygen concentration in the gas sample cell 10. Also, as noted above, these absorption lines need not always appear in the same location since the VCSEL is not "tuned" to the characteristic absorption frequency of the oxygen.

It will be appreciated by those skilled in the art that the foregoing has set forth the presently preferred embodiment of the invention and an illustrative embodiment of the invention but that numerous alternative embodiments are possible without departing from the novel teachings of the invention. For example, while the invention has been described primarily in connection with the measurement of the concentration of oxygen (because of its characteristic absorption lines in the "A" region), those skilled in the art will appreciate that the techniques of the invention may be used to detect other analytes with characteristic absorption spectra in the wavelength range of conventional laser light sources other than VCSELs, e.g., from 500 nm to 2,000 um. All such modifications are intended to be included within the scope of the appended claims.

We claim:

1. A gas analyzer for detecting the concentration of a gaseous component of a gas sample, comprising:

a sample cell containing an unknown concentration of said gaseous component;

a driving circuit which generates a laser driving signal;

a laser light source which outputs laser light that is continuously varied through a range of frequencies including a characteristic absorption frequency of said gaseous component in response to said laser driving signal and that is not locked or tuned to said characteristic absorption frequency of said gaseous component, said continuously varying laser light being directed through said sample cell whereby laser light at said characteristic absorption frequency may be absorbed in proportion to the concentration of said gaseous component in said sample cell;

a detector which detects laser light in said range of frequencies which has passed through said sample cell and which has been absorbed at the characteristic absorption frequency of said gaseous component to provide a detection output; and a compensation circuit which demodulates said detection output to remove said laser driving signal so as to leave an absorption signal with characteristic absorption lines at points in said absorption signal where said laser light source outputs light at said characteristic absorption frequency of said gaseous component, a magnitude of said characteristic absorption lines being proportional to the concentration of said gaseous component in said gas sample.

2. A gas analyzer as in claim 1, further comprising a compensation detector and an optical beamsplitter which splits said continuously varying laser light so that a first portion is directed through said sample cell and a second portion impinges upon said compensation detector, said compensation detector generating a reference signal which is provided to said compensation circuit for removing a common mode signal.

3. A gas analyzer as in claim 1, wherein said sample cell is straight and provides a laminar gas flow path along a central transmission axis of said sample cell from a gas inlet to a gas outlet.

4. A gas analyzer as in claim 3, wherein said laser light source is located at an angle to said central transmission axis of said sample cell at a gas inlet end of said sample cell and said detector is located at an angle to said central transmission axis of said sample cell at a gas outlet end of said sample cell, said sample cell further having reflective walls whereby said continuously varying laser light is reflected by said reflective walls a plurality of times as said laser light passes through said sample cell to said detector.

5. A gas analyzer as in claim 3, further comprising an optical fiber which carries said laser light from said laser light source to a gas inlet end of said sample cell.

6. A gas analyzer as in claim 5, wherein said detector is located on said central transmission axis of said sample cell at a gas outlet end of said sample cell.

7. A gas analyzer as in claim 5, further comprising a highly reflective mirror located on said central transmission axis of said sample cell at said gas outlet end of said sample cell, wherein said detector is located on said central transmission axis of said sample cell at a gas inlet end of said sample cell.

8. A gas analyzer as in claim 1, wherein said laser driving signal is a sawtooth waveform which is applied to said laser light source so as to vary the temperature of a lasing region of said laser light source.

9. A gas analyzer as in claim 2, wherein said laser light source includes a vertical cavity surface emitting laser (VCSEL).

10. A gas analyzer as in claim 9, wherein said laser light source further includes a thermoelectric heater/cooler mounted upon a transistor outline header, said VCSEL being mounted on said heater/cooler and being encased by said header.

11. A gas analyzer as in claim 10, wherein said header includes an optically transmissive window which passes said laser light from said VCSEL to the outside of said header for direction through said sample cell.

12. A gas analyzer as in claim 11, wherein said compensation detector is located on said header so as to receive a portion of said laser light reflected by said optically transmissive window.

13. A gas analyzer as in claim 1, further comprising a processor which calculates the concentration C of said gaseous component from a magnitude $V_A$ of said characteristic absorption lines and a magnitude $V_0$, where $V_0$ is the amount of light at the characteristic absorption frequency of said gaseous component, calculated as if none of said gaseous component is in the sample cell, in accordance with the following equation:

$$C = X \ast V_A / V_0 + Y$$

where X and Y are calibration constants.

14. A gas analyzer as in claim 13, further comprising an electronic device which stores at least said calibration constants X and Y for said laser light source.

15. A method of detecting the concentration of a gaseous component of a gas sample, comprising the steps of:

inserting an unknown concentration of said gaseous component into a sample cell;

generating a laser driving signal;

applying said laser driving signal to a lasing region of a laser light source to cause said laser light source to output laser light that continuously varies through a range of frequencies including a characteristic absorption frequency of said gaseous component and that is not locked or tuned to said characteristic absorption frequency of said gaseous component;

directing said continuously varying laser light through said sample cell whereby laser light at said characteristic absorption frequency may be absorbed in proportion to the concentration of said gaseous component in said sample cell;

detecting laser light in said range of frequencies which has passed through said sample cell and which has been absorbed at the characteristic absorption frequency of said gaseous component to provide a detection output;

demodulating said detection output to remove said laser driving signal so as to leave an absorption signal with characteristic absorption lines at points in said absorption signal where said laser light source outputs light at said characteristic absorption frequency of said gaseous component; and calculating the concentration of said gaseous component in said gas sample from a magnitude of said characteristic absorption lines and a magnitude of said laser driving signal when said laser light source outputs laser light at said characteristic absorption frequency.

16. A method as in claim 15, comprising the additional steps of generating a reference signal and adjusting said detection output with said reference signal so as to remove a common mode signal.

17. A method as in claim 15, wherein said directing step comprises the step of reflecting said continuously varying laser light off of reflective walls of said sample cell a plurality of times as said laser light passes through said sample cell so as to effectively lengthen an optical path through said sample cell.

18. A method as in claim 15, wherein said laser light source is a vertical cavity surface emitting laser (VCSEL), and said applying step includes the step of sweeping said VCSEL through a range of wavelengths by varying a temperature of said lasing region through application of said laser driving signal.

19. A method as in claim 15, wherein said calculating step comprises the step of calculating the concentration C of said gaseous component from said magnitude $V_A$ of said characteristic absorption lines and said magnitude $V_0$, where $V_0$ is the amount of light at the characteristic absorption frequency of said gaseous component, calculated as if none of said gaseous component is in the sample cell, in accordance with the following equation:

$$C = X * V_A / V_0 + Y$$

where X and Y are calibration constants.

* * * * *

UNITED STATES PATENT AND TRADEMARK OFFICE
CERTIFICATE OF CORRECTION

PATENT NO. : 6,091,504
DATED : 7/18/00
INVENTOR(S) : Walker et al

It is certified that error appears in the above-identified patent and that said Letters Patent is hereby corrected as shown below:

Col. 11, line 3, change "10" to --110--. (PTO)

Signed and Sealed this

Seventeenth Day of April, 2001

Attest:

NICHOLAS P. GODICI

*Attesting Officer*  *Acting Director of the United States Patent and Trademark Office*